(12) United States Patent
Dziedzic et al.

(10) Patent No.: US 7,642,076 B2
(45) Date of Patent: Jan. 5, 2010

(54) PROCESS FOR IMMOBILIZATION OF PROTEIN CATALYSTS, PRODUCT, AND USE

(75) Inventors: Daniel Dziedzic, Rochester Hills, MI (US); John T Johnson, Sterling Heights, MI (US); Kenneth B Gross, Troy, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 909 days.

(21) Appl. No.: 10/841,283

(22) Filed: May 7, 2004

(65) Prior Publication Data

US 2005/0250193 A1    Nov. 10, 2005

(51) Int. Cl.
*C12N 11/16* (2006.01)
*C12N 9/00* (2006.01)

(52) U.S. Cl. .................................... 435/174
(58) Field of Classification Search ........................ None
See application file for complete search history.

(56) References Cited

U.S. PATENT DOCUMENTS

| 4,246,351 | A | * | 1/1981 | Miyake et al. | ............... | 435/182 |
|---|---|---|---|---|---|---|
| 5,280,061 | A | | 1/1994 | Haraguchi et al. | | |
| 5,445,920 | A | | 8/1995 | Saito | ........................ | 430/311 |
| 6,682,942 | B1 | * | 1/2004 | Wagner et al. | ................. | 506/9 |
| 6,721,587 | B2 | | 4/2004 | Gough | ....................... | 600/345 |
| 2004/0182723 | A1 | * | 9/2004 | Saito et al. | ............... | 205/777.5 |

FOREIGN PATENT DOCUMENTS

| EP | 0 291 130 | | 11/1988 |
|---|---|---|---|
| JP | 61-187792 | * | 8/1986 |

OTHER PUBLICATIONS

NPL-Definition of polyvinyl chloride (PVC), pp. 1-3. Accessed Aug. 18, 2008.*
NPL-Definition of adhesive, pp. 1-5. Accessed Aug. 18, 2008.*
NPL-Full range or Silanes from www.dowcorning.com/content/silanes/fullrangeofsilanes.asp, pp. 1-2. Accessed Aug. 18, 2008.*
NPL-English abstract of JP-61-187792 from EAST, pp. 1-2, Aug. 1986.*
Trasnlation of JP1986187792, Aug. 21, 1986.*
Fatma A. Simsek-Ege et al., "Polyelectrolyte Cages for a Novel Biometric CO2 Sequestration System," Fuel Chem. Div. Preprints 2001, 46(1), pp. 56-60.
Iqbal Gill et al., "Lipase-Silicone Biocomposites: Efficient and Versatile Immobilized Biocatalysts, " J. Am. Chem. Soc., vol. 121, No. 41, pp. 9487-9496 (1999).
Mark, H.F., "Adhesive Compositions," Encyclopedia of Polymer Science and Technology (2d ed.) vol. 1, pp. 569-574.
Shin-ichiro Suye et el., "Immobilization of glucose oxidase on poly-(L-lysine)-modified polycarbonate membrane," Biotechnol. Appl. Biochem. (1998) vol. 27, pp. 245-248.

* cited by examiner

*Primary Examiner*—Cecilia Tsang
*Assistant Examiner*—Julie Ha
(74) *Attorney, Agent, or Firm*—Harness, Dickey & Pierce P.L.C.

(57) ABSTRACT

An immobilized protein catalyst is prepared by applying an adhesive to a polymeric support, applying a layer of a globular protein over the layer of adhesive, binding a crosslinking agent to the protein layer, and binding the protein catalyst by reaction with the crosslinking agent.

13 Claims, 3 Drawing Sheets

PROCESS FOR IMMOBILIZATION OF PROTEIN CATALYSTS, PRODUCT, AND USE

FIELD OF THE INVENTION

The present invention relates generally to methods of immobilizing protein catalysts onto solid surfaces. In another aspect, the invention relates to plastic supports bearing protein catalysts.

BACKGROUND OF THE INVENTION

Protein catalysts, or enzymes, are useful in promoting reactions in various applications. For certain applications the enzyme must be immobilized on a suitable solid support. Immobilization may be accomplished by a variety of chemically-based approaches including adsorptive, ionic bonding, and covalent bonding techniques. Additionally, the catalyst may be entrapped in a gel or polymer matrix, stabilized in a micellar structure, incorporated into the substance of the matrix itself, or enclosed in a membrane using the so-called membrane-enclosed enzyme catalysis technique.

The immobilization procedures are, as a whole, difficult, expensive, and often only partially effective. For instance, one method requires soaking a polycarbonate membrane for 24 hours in a solution of poly-(L-lysine), rinsing, soaking the membrane in a buffered glutaraldehyde solution for 2 hours, washing, and finally soaking the membrane in a buffered glucose oxidase solution for 24 hours. This method relies on covalent bonding between the poly(L-lysine) layer and the polycarbonate membrane. This method is not effective unless the support medium and the poly(L-lysine) layer are capable of covalent bonding with each other. Another method immobilizes lipases by formation of enzyme-silicone polymer composites. This paper describes problems with binding to hydrophobic polymer surfaces, low catalyst densities in sol-gel entrapment methods, and limited application of crosslinked lipase preparations. To address these issues the paper describes adsorption of proteins onto poly(hydroxymethylsiloxane) [PHOMS], followed by reaction with silanol-terminated PDMS prepolymers, poly(diethylsilicate), and (3-aminopropylethoxysilane) crosslinker to form a solid silicone rubber with encapsulated lipase-PSOMS. Polysiloxanes are relatively expensive, however, and may not be a suitable support for many applications.

The goal in developing new methods of immobilizing enzymes is to enhance the ease, economy, and simplicity of achieving high enzymatic activity that persists for long periods of time at a defined location on a fixed surface or support. To achieve this goal it is desirable to have as high of a catalytic activity of an immobilized enzyme as possible and for the catalytic activity to be relatively stable. It would also be desirable to have a method of immobilizing an enzyme on a polymeric support that would be useful with many kinds of supports and enzymes.

SUMMARY OF THE INVENTION

A method of immobilizing a protein catalyst on a polymeric support has steps of (a) applying an adhesive, particularly a one-component adhesive in organic solution, to the polymeric support; (b) applying a layer of a globular protein over the layer of adhesive; (c) binding a crosslinking agent to the protein layer; and (d) binding the protein catalyst by reaction with the crosslinking agent In a further embodiment of the invention, a one-component, solvent-based adhesive is applied in the first step.

In still a further embodiment of the invention, the crosslinking agent has a plurality of groups reactive with active hydrogens, particularly hydrogens of amine groups. In a particularly preferred embodiment, the crosslinking agent is or includes a di-aldehyde, especially glutaraldehyde.

The immobilized protein has stable catalytic activity, for dry and moist storage and for ambient and refrigerated storage.

The invention further provides an article having an immobilized protein catalyst on a solid support prepared by the method of the invention.

Depending on the choice of protein catalyst, the immobilized protein catalyst may be used, for example, to enhance absorption of carbon dioxide into liquids, make renewable fuels from biomass, make bioplastics and "smart materials" such as biomaterials that undergo controlled transformations that can be used for sensing, actuating, and controlling chemical and physical functions, destroy contaminants in machining fluids, purify indoor air, or act as a biosensor for a given organic molecule. For instance, immobilized carbonic anhydrase can be used to hydrate carbon dioxide to carbonic acid for sequestering carbon dioxide.

Our invention takes advantage of advances in adhesive chemistry to modify an established technique to produce a simple, economical, four-step process for cost-effective enzyme immobilization.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates a possible variation of up to 5% in the value.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
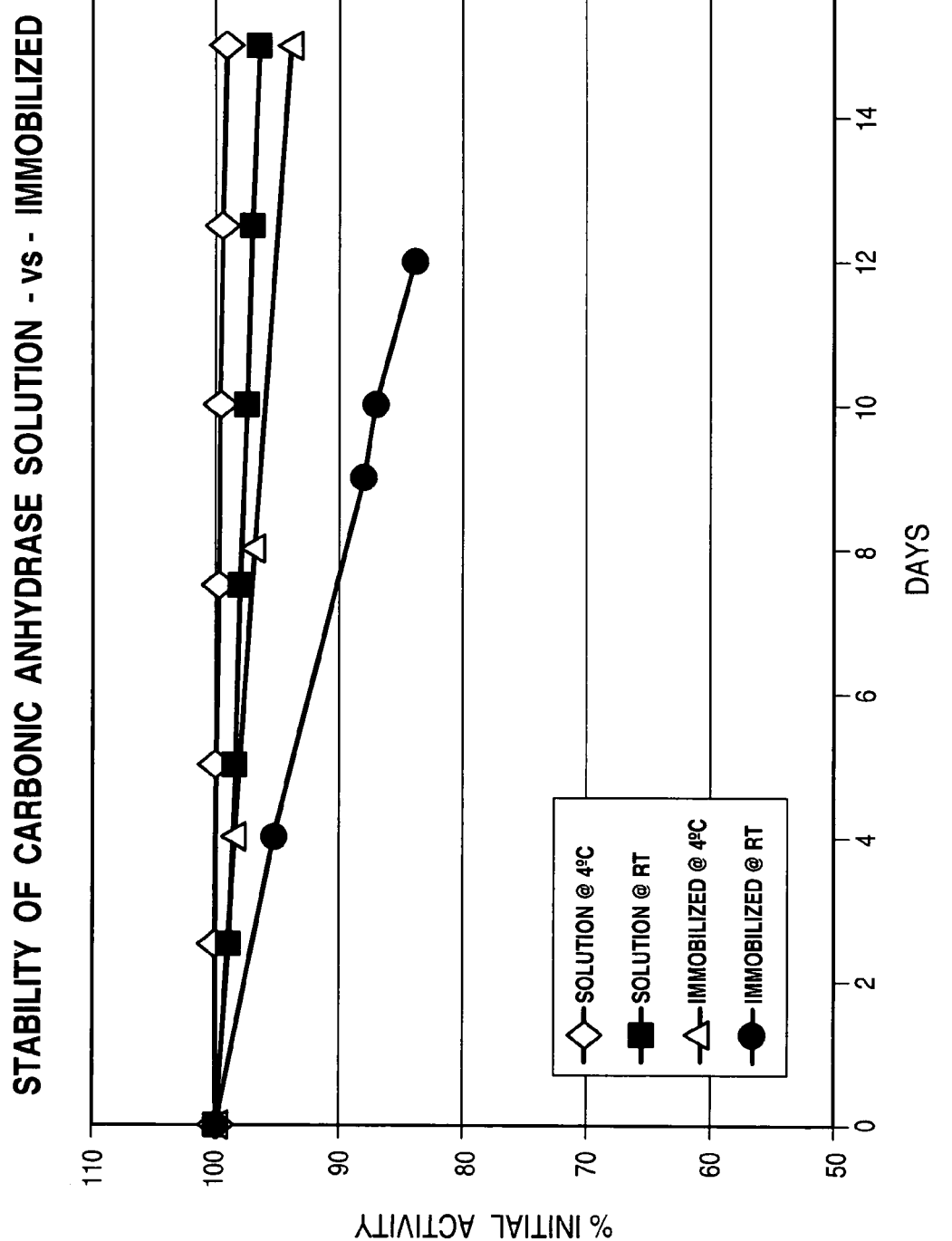
FIG. 1 is a graph showing activity over time of a protein catalyst in solution compared the same protein catalyst immobilized on a support according to the invention at room temperature and at 4° C.

The following description of the preferred embodiment(s) is merely exemplary in nature and is in no way intended to limit the invention, its application, or uses.

A support, which may be selected from any useful material including polymeric, cardboard, glass, metal, and foam core materials, of a desired design or shape is used to support the protein catalyst. The support may be selected, for example, from any polymeric material appropriate for the conditions under which the catalyst will be used. In general, supports formed from polyethylene, polypropylene, polybutadiene, polyamide, polycarbonate, vinyl polymers, polypropylene glycol, polyesters such as poly(ethylene terephthalate), phenolic polymers, epoxy polymers, polyurethanes, and so on. Useful vinyl polymers may be homopolymers and copolymers of, for example, α,β-ethylenically unsaturated monocarboxylic acids containing 3 to 5 carbon atoms and α,β-ethylenically unsaturated dicarboxylic acids containing 4 to 6 carbon atoms, and derivatives of these such as esters and amides; vinyl esters, vinyl ethers, vinyl ketones, and aromatic or heterocyclic aliphatic vinyl compounds. Suitable examples of vinyl polymers include, without limitation, poly(methyl methacrylate), other acrylic polymers, poly(vinyl chloride), poly (vinyl acetate), styrene polymers and copolymers, and so on.

The support may have a shape adapted to the needs of a particular application for which the immobilized catalyst will be employed. For example, the supports can be discs, sheets, rods, cones, spheres, cylinders, membranes and so forth.

An adhesive is applied to the surface of the support. It is preferred to use a one-component, solvent-based adhesive. Such adhesives are known and readily available commercially. Such adhesives include PVC and acrylic adhesives such as described in "Adhesive Compositions," *Encyclopedia of Polymer Science and Technology* (2d ed.) Vol. 1, pages 569-74, incorporated herein by reference and described in more detail herein and those described, for example, in Haraguchi et al., U.S. Pat. No. 5,280,061 and the documents mentioned therein, all of which are incorporated herein by reference. One suitable adhesive that is commercially available is 3M® PHOTO MOUNT™ spray adhesive, which readily adheres to different kinds of materials, including plastics such as polypropylene, and binds the globular protein layer thereto.

Suitable acrylic adhesives can be derived from acrylate or methacrylate ester monomers, while other monomers can optionally be added to convey special properties or assist in cross-linking of the polymeric adhesive. Both polyacrylate solutions and emulsions can be used as suitable adhesives. In addition to the preformed polymers, there are several versions of the acrylics in the form of polymerizing or curing types of adhesives; these include cyanoacrylates, anaerobic adhesives, and reactive acrylic structural adhesives. The glass-transition temperature ($T_g$) of an acrylic polymer is a key consideration in designing adhesives. For example, acrylates that have more than four carbon atoms in the ester alkyl group yield polymers with low glass transition temperature ($T_g$); as where methacrylates tend to yield higher $T_g$ homopolymers. Low $T_g$ has been correlated with a high degree of tackiness in acrylic polymers. Acrylic adhesive products with $T_g$ ranging from –60° C. to greater than 30° C. are commercially available. All of these materials are copolymers, many with acrylic acid or other polar monomers added to increase adhesion. A general characteristic of acrylic adhesives is stability to light and heat. Additionally, cross-linking can be used to enhance solvent resistance and increase cohesive strength of such acrylic adhesives. Some emulsion polymers are cross-linked during polymerization, but it is common to subsequently add cross-linking agents, such as amino resins, polyisocyanates, epoxies, or phenolics to achieve cross-linking in the adhesive. In systems that employ such additives, the acrylic copolymer contains a reactive functional group that reacts with the crosslinking agent, such as carboxyl or hydroxyl.

A large and important group of acrylic adhesives contain monomers, such as N-methylolacrylamide or N-butoxymethylacrylamide, which induce cross-linking upon heating. A common practice is to add a small amount of a soluble cation to effect cross-linking after drying; such as salt additives like zinc acetate for emulsions, and titanium alkoxides or aluminum acetylacetonate for solutions. Both higher $T_g$ and lower $T_g$ (e.g., tacky) polymeric adhesives can be used for bonding plastic or polymers, and such acrylic adhesives are well know for use as pressure-sensitive adhesives.

Non-limiting examples of acrylic adhesives include those containing principal monomers of butyl, 2-ethylhexyl, or octyl acetate, and may further contain polar monomers, such as acrylic acid, acrylamide, or dimethylaminoethyl methacrylate, as well as modifying monomers such as vinyl acetate, ethyl acrylate, or methyl methacrylate. In certain aspects, a suitable monomer for the acrylic adhesive for cross-linking can be N-methylol. For example, a typical general-purpose pressure-sensitive acrylic adhesive is derived from a monomer feed of 75 parts 2-ethylhexyl acrylate, 23 parts vinyl acetate, and 2 parts acrylic acid. Unless cross-linked after application, the pressure-sensitive adhesives are of sufficient molecular weight to ensure adequate cohesive strength.

Three additional kinds of acrylic adhesives, namely cyanoacrylates, anerobic adhesives, and two-part structural acrylics, begin with monomers or oligomers, which polymerize in the bond line. Principal cyanoacrylate commercially-available adhesives comprise ethyl and/or methyl ester monomers, although several other types of monomers are commercially available, as well. Such monomers readily undergo anionic polymerization by exposure to one or more bases. Stabilization of these reactive liquid monomers is typically done by including various acidic materials, typically sulfonic acids. Free-radical inhibitors can also be added since cyanoacrylates will undergo radical polymerization. To improve heat resistance, hydrolytic instability, and brittleness, various well known modifiers can be added, particularly those that increase toughness or other monomers, such as acrylates or allyl compounds to yield thermosets, which result in more solvent and heat-resistant adhesives. In addition, some formulations may contain dissolved polymers to increase viscosity. Cyanoacrylates are widely available and generally provide rapid curing and good adhesion to elastomers and many plastics.

Anaerobic acrylic adhesives generally exhibit shelf life in the presence of air (e.g., oxygen), but cure or polymerize when confined in a bond line, where oxygen is absent. An exemplary composition of an anaerobic adhesive comprises a dimethacrylate of a polyethylene glycol, such as tetraethylene glycol, and optionally contains cumene hydroperoxide (CHP), a dimethylaniline derivative and saccharin as an initiator system. Reductants, such as those containing copper ions, can be applied to inactive surfaces prior to applying an anaerobic acrylic adhesive to enhance curing. One example of an anaerobic acrylic adhesive comprises urethane-based methacrylate oligomers, where the molecular weight may be as high as 1500, instead of the more fluid glycol dimethacrylates, where the curing mechanism is more similar to that of conventional two-part structural acrylic resins.

Reactive acrylics (e.g., two part acrylics) include toughened acrylics and may comprise free-radical polymerizing monomers, an elastomer or oligomer as reinforcement or toughening agent, and a redox system to initiate curing. Such two-part reactive acrylic adhesives are typically formulated for very rapid cure, thus, a reductant portion of the redox system (e.g., the activator or accelerator), is stored separately from the oxidant or initiator part (which tends to be mixed with the monomer-elastomer mixture). In most cases, the activator is applied from a volatile solvent to one adherend surface, and the adhesive is applied to the other adherend surface. When the accelerator is dry, the two surfaces are mated and then the monomers polymerize and cure within a short amount of time (e.g., on the order of minutes). One well known two-part acrylic adhesive includes methyl methacrylate as the principal monomer, chlorosulphonated polyethylene as an elastomer component, CHP as an initiator, and an activator including an amine-aldehyde condensation product dissolved in a chlorinated solvent, which was developed by DuPont. Methacrylic acid can be employed as a component in such a system, because it is beneficial with such a redox system. Other suitable reactive acrylic adhesives include those where an aromatic amine reductant is included in the monomer-elastomer mix and a peroxide-containing compound as an activator. Other commercially available variations include those using urethane-based dimethacrylate oligomers, ultraviolet-curable acrylic adhesives using photoinitiators in lieu of peroxide.

Polyamides based on dimer acids can be used as acrylic adhesives that form single component hot melt adhesives. Unlike the reactive polyamides, which are epoxy co-reactants, the hot-melt type can be produced from a stoichiometric ratio of amine and carboxyl function. In addition, a number of hot-melt polyamides are produced by copolymerization of multiple diacids or diamines, or both, to obtain complex polymers with lower melting or softening points. Although more commonly utilized as hot melts, polyamides can also be applied from solution; mixed solvents containing alcohols are used, since solubility parameters of 10 to 12 are characteristic of these polymers. The dimer acid-based polyamides can be applied to a broad range of substrates because of the presence of both the polar amide group and long hydrocarbon sequences furnished by the acid. Thermoplastic polyamides are produced in various molecular-weight ranges with consequent variation in melt viscosity, modulus, impact and tensile strength, and softening points that range from less than 100° C. to about 200° C. Various thermoplastic resins and tackifiers can also be added to such polyamide adhesives to further improve adhesion to certain substrates. For example, incorporation of amorphous polypropylene in a dimer acid-based polyamide leads to markedly enhanced peel adhesion to acrylic sheets and adding phenolic resin produces much higher peel adhesion to ABS plastic.

Like polyamide adhesives, polyester hot-melt adhesives can be prepared by copolymerization of multiple di-acids or glycols, or both, chosen to lower adhesive melting points or to obtain amorphous polymers. Many formulations are based on mixtures of terephthalic with other aromatic dicarboxylic acids or mixtures of aromatic and aliphatic acids; other compositions use mixtures of glycols, mixed acids, and/or both mixed acids and glycols. Such blends of polyester optionally comprise novolak resins. Conventional modifying additives and fillers may optionally be used in these copolymer adhesive compositions.

It is desirable for the adhesive to be diluted in solvent so that it is easier to apply a thin layer to the support surface. The adhesive may be diluted in an appropriate organic solvent, for example and without limitation hexane, heptane, toluene, xylene, methylene chloride, carbon tetrachloride, trichloromethane, Aromatic 100, tetrahydrofuran, acetone, 2-propanol, methanol, and acetonitrile. It is preferred to apply the adhesive by dip coating the support, although it is possible to apply the adhesive by other means, such as spraying, brushing, roll coating, and so on.

After applying the adhesive, it is preferred to evaporate any solvent in the adhesive layer. The drying step may be carried out at room temperature in air.

A globular protein layer is then applied onto the adhesive layer. The globular protein layer and the crosslinker are selected to provide appropriate interaction with the enzyme being immobilized. Globular proteins include albumins, globulins, histones, and protamines. It is particularly preferred to use an albumin, especially ovalbumin, which is derived from avian eggs, a readily available source.

The globular protein layer may be applied by immersing the support with adhesive layer into a buffered solution of the protein. The pH of the solution is preferably substantially neutral, although pH may differ somewhat from 7.0 depending on the globular protein selected. The solution may be diluted to apply a layer of appropriate thickness. A more dilute solution will deposit a thinner protein layer. The protein layer need only be thick enough so that the crosslinker is anchored to the support densely enough to achieve the desired surface concentration of enzyme. In general, a solution that is about 0.5% to about 5.0% is sufficiently concentrated. More concentrated solutions would also work, but would make a thicker layer of the globular protein on the support.

The support with adhesive layer may be dipped one or more times in the globular protein solution for a desired time, preferably from about 1 to about 5 seconds. The globular protein may be kept chilled, e.g. at 4° C., if needed to prevent denaturation and/or contamination with microbes. The deposited globular protein layer may then be allowed to dry.

A crosslinking agent is attached to the globular protein layer to provide a site for immobilizing the enzyme. The crosslinking agent has at least two groups, one group that can attach to the globular protein layer and a second group that can attach to the enzyme. In general, the globular protein layer and/or enzyme may be bound through reaction of an amine group, acid group, phenolic group, sufhydryl group, or imidazole group, so that the crosslinking agent may have functionality such as aldehyde groups, isocyanate groups, oxirane groups, thio groups, sulfhydryl groups, amine groups, and photoreactive crosslinkers. Known crosslinking agents include, without limitation, polyaldehydes such as glutaraldehyde; polyisocyanates such as 1,6-diisocyanatohexane (hexamethylene diisocyanate or HMDI), 1,4-butylene diisocyanate, lysine diisocyanate, 1,4-methylene bis-(cyclohexyl isocyanate), toluene diisocyanate (toluene diisocyanate or TDI), isophorone diisocyanate (IPDI), $\alpha,\alpha,\alpha',\alpha'$-tetramethyl xylylene diisocyanate (TMXDI) and 4,4'-dibenzyl diisocyanate; bisdiazobenzidine; hexamethylene diisothicyanate; hexamethylene diamine; polyepoxides such as polyoxyethylene-bis(glycidyl ether); N,N'-ethylene bis-maleimide; N,N'-polymethylene bisiodoacetamide; 4-azido-benzoic acid (3-sulfo-N-succinimidyl) ester sodium salt; 1,4-bis[3-(2-pyridyldithio)propionamido]butane; bis[2-(N-succinimidyl-oxycarbonyloxy)ethyl]sulfone; bis[2-(4-azidosalicylamido)ethyl]disulfide; dimethyl 3,3'-dithiopropionimidate dihydrochloride; ethylene glycol disuccinate di(N-succinimidyl) ester; and sebacic acid bis(N-succinimidyl)ester. The crosslinking agent is selected so that the bonding to the globular protein layer and the bonding of the protein catalyst both take place under conditions that avoid denaturing the protein catalyst.

The crosslinker may be applied by any known method. For example, the coated support may be immersed for an hour or two in a solution of the crosslinker in an aqueous buffer. The solution should be of an appropriate concentration to allow a layer of crosslinker to adhere to the globular protein surface. Again, the pH of the solution may be substantially neutral. The deposited crosslinker layer may then be rinsed with deionized water and allowed to dry.

Many different protein catalysts are known and commercially available. Among those that may be used are carbonic anhydrase (which catalyzes the hydration of carbon dioxide to carbonic acid), papain, alpha-amylase, ribonuclease, trypsin, alpha-chymotrypsin, aminoacylase, aldolase, alcohol dehydrogenase, glutamate dehydrogenase, glucose oxidase, tyrosinase, catalase, peroxidase, carboxypepsidase A, alkaline phosphatase, lysozyme, subtilisin, and others. A combination of protein catalysts may be used.

The protein catalyst may be applied from a solution of the protein catalyst in an aqueous buffer, e.g. a phosphate buffer. The conditions are appropriate to avoid denaturing the enzyme or protein layer. The solution may be chilled, for example to 4° C., to avoid denaturation and/or biological contamination. The time necessary to attain the desired catalytic activity for a given protein catalyst may be determined in a straightforward manner by measuring the catalytic activity at timed intervals.

The invention is further described in the following example. The example is merely illustrative and does not in any way limit the scope of the invention as described and claimed. All parts are parts by weight unless otherwise noted.

EXAMPLE 1

Immobilized Carbonic Anhydrase

A polypropylene disk 0.25 inches in diameter, 0.0625 inches thick was dipped for several seconds in an adhesive solution prepared from 1 part by volume of 3M® PHOTO MOUNT™ spray adhesive diluted in 3 parts by volume toluene, then further diluted in 3 parts by volume hexane. The disk was removed from the adhesive and allowed to dry. The dried disk was then dipped in a freshly prepared mixture of about 1 part by volume ovalbumin and 10 parts by volume of 50 mM phosphate buffer, pH 7.0. The ovalbumin adhered readily to the adhesive layer. The disk was then air dried. Next, the disk was immersed for 2 hours in a solution held at 4° C. of glutaraldehyde, 1% by weight, in 50 mM phosphate buffer, pH 7.0. The disk was then washed three times with distilled water and air dried. Finally, the disk was incubated with carbonic anhydrase by immersing the disk in a 10 mg/ml solution of carbonic anhydrase in the 50 mM phosphate buffer for 2 hours at 4° C. The disk was then removed and rinsed with the phosphate buffer.

The immobilized protein has excellent stability. Carbonic anhydrase disks prepared in this way could be stored dry or moist, chilled or at room temperature with minimal loss of activity. Referring now to the figures, FIG. 1 is a graph comparing stability of carbonic anhydrase stored in a solution at room temperature or at 4° C. and compares it with the stability of immobilized carbonic anhydrase attached with glutaraldehyde to an ovalbumin layer prepared using the method described in Example 1. Samples of the immobilized carbonic anhydrase were stored at room temperature and at 4° C., and the activity was followed over a period of 10-15 days. The activity was measured spectrophotometrically by p-nitrophenylacetate assay using the method described by Simsek-Ege et al. in "Polyelectrolyte Cages for a Novel Biomimetic $CO_2$ Sequestration System," Fuel Chemistry Division Preprints 2001, 46(1), pp. 56-60. As the graph demonstrates, the activity of the protein catalyst changed very little under these conditions.

Figure 2:
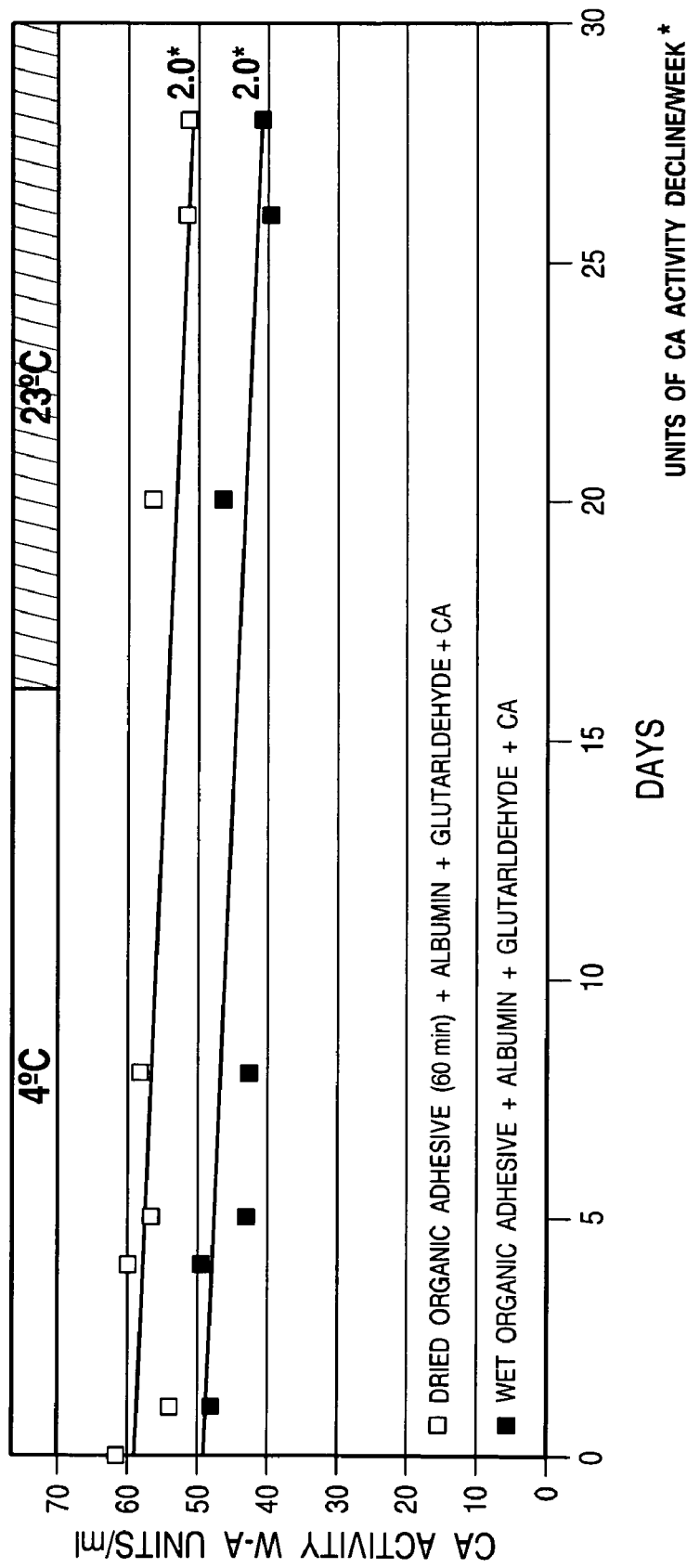
FIG. 2 is a graph comparing stability of an immobilized protein catalyst on a rough polypropylene disk according to the invention for globular protein layers applied over dried adhesive and wet adhesive stored initially at 4° C. and then stored at room temperature.

FIG. 2 is a graph comparing stability of immobilized carbonic anhydrase attached with glutaraldehyde to an ovalbumin layer prepared using the method described in Example 1 on a rough polypropylene disk. Separate polypropylene disks were prepared in which the ovalbumin layers were applied over dried adhesive and wet adhesive. The graph shows that the disk made by drying the adhesive before applying the protein layer had a higher initial catalytic activity, but that catalytic activity decreased at the same rate for both disks.

Figure 3:
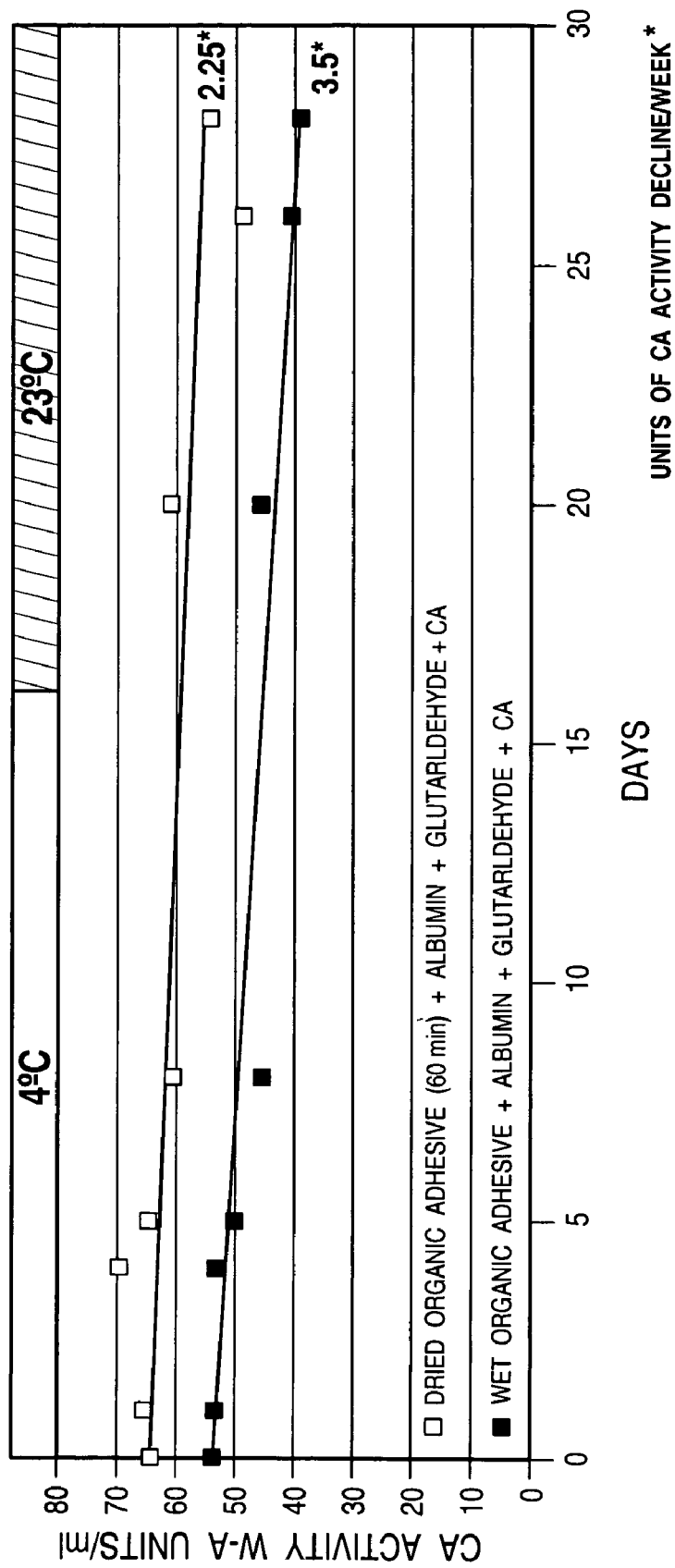
FIG. 3 is graph comparing stability of an immobilized protein catalyst on a smooth polypropylene disk according to the invention for globular protein layers applied over dried adhesive and wet adhesive stored initially at 4° C. and then stored at room temperature.

FIG. 3 is a graph comparing stability of immobilized carbonic anhydrase attached with glutaraldehyde to an ovalbumin layer prepared using the method described in Example 1 on a smooth polypropylene disk. Separate polypropylene disks were prepared in which the ovalbumin layers were applied over dried adhesive and wet adhesive. The graph shows that the same high efficiency obtained with the rough surface could be obtained using a smooth surface without chipping or curling of the adhesive layer.

The immobilized carbonic anhydrase can be used to hydrate carbon dioxide to carbonic acid for sequestering carbon dioxide. The catalytic support may be prepared by immersing a polymeric membrane, such as a polypropylene membrane, beads, fabrics, fibers, membranes, particulates, porous surfaces, rods, tubes, or supports of other shape in an adhesive solution prepared from 1 part by volume of 3M® PHOTO MOUNT™ spray adhesive diluted in 3 parts by volume toluene, then further diluted in 3 parts by volume hexane. The adhesive is dried, then dipped in a freshly prepared mixture of about 1 part ovalbumin and 10 parts of a phosphate buffer solution to add a layer of globular protein. The protein layer is then treated with a crosslinker such a glutaraldehyde, 1% by weight in phosphate buffer solution, and finally carbonic anhydrase is attached by the crosslinker from a solution of carbonic anhydrase in phosphate buffer. The support bearing the immobilized carbonic anhydrase may then be placed into an aqueous medium where it is exposed to carbon dioxide in order to facilitate hydration of the carbon dioxide to carbonic acid.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of preparing an immobilized protein catalyst, comprising steps of
   (a) applying a polymeric adhesive to a polymeric support to adhere said polymeric support to a globular protein layer;
   (b) applying a layer of a globular protein over the layer of adhesive to form said globular protein layer;
   (c) binding a crosslinking agent to the protein layer; and
   (d) reacting a protein catalyst with the crosslinking agent thereby binding said protein catalyst to said crosslinking agent to immobilize said protein catalyst on said polymeric support.

2. A method of preparing an immobilized protein catalyst according to claim 1, comprising applying a one-component, solvent-based polymer adhesive in step (a).

3. A method of preparing an immobilized protein catalyst according to claim 1, comprising applying a crosslinking agent having a plurality of groups reactive with a member selected from the group consisting of amine groups, carboxylic acid groups, phenolic groups, sufhydryl groups, and imidazole groups.

4. A method of preparing an immobilized protein catalyst according to claim 1, comprising applying a crosslinking agent having a plurality of groups reactive with hydrogens of amine groups in step (c).

5. A method of preparing an immobilized protein catalyst according to claim 1, wherein the adhesive applied in step (a) is dried before step (b).

6. A method of preparing an immobilized protein catalyst according to claim 1, wherein the polymeric support comprises a member selected from the group consisting of polyethylene, polypropylene, polybutadiene, polyamide, polycarbonate, vinyl polymers, polypropylene glycol, polyesters, phenolic polymers, epoxy polymers, polyurethanes, acrylic polymers, styrene polymers and copolymers, and combinations thereof.

7. A method of preparing an immobilized protein catalyst according to claim 1, wherein the adhesive is applied as a dilute solution.

8. A method of preparing an immobilized protein catalyst according to claim 7, wherein the adhesive is diluted in organic solvent selected from the group consisting of hexane, heptane, toluene, xylene, methylene chloride, carbon tetrachloride, trichloromethane, Type I light aromatic naphtha (Aromatic 100), tetrahydrofuran, acetone, 2-propanol, methanol, acetonitrile, and combinations thereof and wherein the adhesive is applied in step (a) by dipping the support into the adhesive diluted in organic solvent.

9. A method of preparing an immobilized protein catalyst according to claim 1, wherein the globular protein comprises an albumin.

10. A method of preparing an immobilized protein catalyst according to claim 1, wherein the globular protein comprises ovalbumin.

11. A method of preparing an immobilized protein catalyst according to claim 1, wherein the crosslinking agent has a plurality of aldehyde groups, isocyanate groups, oxirane groups, thio groups, sulfhydryl groups, amine groups, or photoreactive groups.

12. A method of preparing an immobilized protein catalyst according to claim 1, wherein the crosslinking agent comprises glutaraldehyde.

13. A method of preparing an immobilized protein catalyst according to claim 1, wherein the protein catalyst comprises carbonic anhydrase.

* * * * *